United States Patent [19]

Lam

[11] 4,071,318

[45] Jan. 31, 1978

[54] TEST COMPOSITION AND DEVICE FOR DETERMINING PEROXIDATIVELY ACTIVE SUBSTANCES

[75] Inventor: Charles Tak Wai Lam, Elkhart, Ind.

[73] Assignee: Miles Laboratories, Inc., Elkhart, Ind.

[21] Appl. No.: 777,005

[22] Filed: Mar. 14, 1977

[51] Int. Cl.² .................... G01N 31/22; G01N 33/16
[52] U.S. Cl. ........................... 23/253 TP; 23/230 B; 252/408
[58] Field of Search ................ 23/253 TP, 230 B; 252/408

[56] References Cited

U.S. PATENT DOCUMENTS

| | | | |
|---|---|---|---|
| 3,012,976 | 12/1961 | Adams, Jr. et al. | 23/230 B X |
| 3,252,762 | 5/1966 | Adams, Jr. et al. | 23/253 TP |
| 3,853,470 | 12/1974 | Morin et al. | 252/408 X |
| 3,853,471 | 12/1974 | Rittersdorf et al. | 23/253 TP |
| 3,917,452 | 11/1975 | Rittersdorf et al. | 23/230 B |
| 4,017,261 | 4/1977 | Svoboda et al. | 252/408 X |

*Primary Examiner*—Robert M. Reese
*Attorney, Agent, or Firm*—E. H. Gorman

[57] ABSTRACT

A test composition and device are disclosed for determining the presence of peroxidatively active substances, such as hemoglobin, in a test sample. Also disclosed is a one-dip method for preparing the device.

The test composition comprises:
  an organic hydroperoxide,
  an indicator capable of producing a detectable response in the presence of a hydroperoxide and a peroxidatively active substance, and
  a borate ester having the structure

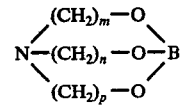

in which $m$, $n$ and $p$, same or different, are integers of 1 to about 4.

The test device comprises a carrier matrix incorporated with the test composition.

30 Claims, No Drawings

TEST COMPOSITION AND DEVICE FOR DETERMINING PEROXIDATIVELY ACTIVE SUBSTANCES

BACKGROUND OF THE INVENTION

1. Field of the Invention

The present invention relates to the detection of constituents in a test sample. More particularly, the invention relates to the qualitative and semi-quantitative analysis of a sample for constituents which possess peroxidative activity.

2. Description of the Prior Art

Many analytical methods are presently available for detecting the presence of peroxidatively active substances in samples such as urine, fecal suspensions, and gastrointestinal contents. Hemoglobin and its derivatives are typical of such "peroxidatively active" substances because they behave in a manner similar to the behavior of the enzyme peroxidase. Such substances have also been referred to as pseudoperoxidases. Peroxidatively active substances are enzyme-like in that they catalyze the redox reaction between peroxides and benzidine, o-tolidine, 3,3',5,5'-tetramethylbenzidine, 2,7-diaminofluorene or similar indicator substances, thereby producing a detectable response such as a color change. Hence, most methods for determining the presence of occult blood in test samples rely on this pseudoperoxidase activity.

Several methods have evolved over the years which rely on enzyme-like catalysis of the peroxidic oxidation of color-forming indicators. Primarily these include wet chemical procedures and "dip-and-read" type reagent-bearing strips. Of the former, a typical example is set forth in Richard M. Henry, et al., *Clinical Chemistry Principles and Techniques* (Hagerstown, Maryland: Harper and Row, 1974), pp. 1124–1125. This procedure involves the use of glacial acetic acid (buffer), diphenylamine (indicator), and hydrogen peroxide. While such wet methods have proven analytical ability, they are nevertheless fraught with obvious shortcomings, not the least of which are poor reagent stability and inadequate sensitivity. Inherent to such reagent solutions is a decline in stability (ergo sensitivity) so rapid that fresh reagent solutions must be prepared after several days of storage, a necessity resulting in both excessive time required of analytical personnel, and poor economy because of having to waste costly reagents.

A second method for the determination of peroxidatively active substances, and the one presently preferred by most clinical assayists and analysts, is the use of so-called "dip-and-read" reagent strips. Typical of such devices is a reagent strip manufactured by the Ames Company Division of Miles Laboratories, Inc. and sold under the name HEMASTIX®. This reagent strip comprises, in essence, a porous paper matrix affixed to a plastic strip or handle. The matrix is incorporated with a buffered mixture of an organic hydroperoxide and o-tolidine. Upon immersion in a liquid containing hemoglobin, myoglobin, erythrocytes or other pseudoperoxidases, a blue color develops in the matrix, the intensity of which is proportional to the concentration of the peroxidatively active substance in the sample. Thus, by comparing the color developed in the matrix to a standard color chart, the assayist can determine, on a semi-quantitative basis, the amount of unknown present in the sample.

Hence, the advantages of reagent strips over wet chemistry methods are predominantly twofold: strips are easier to use because neither the preparation of reagents nor the attendant apparatus are required; and greater stability of reagents is afforded, resulting in greater accuracy, sensitivity and economy.

But the inherent advantages of strips over wet chemistry notwithstanding, certain characteristics of presently available strips are in need of improvement. These are stability and sensitivity. Whereas these properties in current state-of-the art strips for determining pseudoperoxidases are greatly enhanced over those of wet chemical methods, there would nevertheless accrue a great advance in the art if such strips could be made even more stable during storage and even more sensitive to peroxidatively active substances. It was towards achieving these improvements that the research activities resulting in the present invention were directed.

At least three attempts at achieving the above-mentioned goals are recorded in the prior art. A recitation in *Chemical Abstracts* Volume 85, page 186 (1976) describes a two-dip method for preparing reagent strips containing o-tolidine and phenylisopropyl hydroperoxide. In this method a solution is made of the indicator (o-tolidine · 2HCl) and polyvinylpyrrolidone in ethanol). To this solution were added a small amount of surfactant and enough citrate buffer to provide a pH of 3.7. Filter paper strips impregnated with ethyl cellulose were dipped in this solution and dried. The thus-impregnated filter paper was subsequently dipped into a second solution containing 1,4-diazabicyclo [2.2.2]octane, phenylisopropyl hydroperoxide and polyvinylpyrrolidone dissolved in an ethanol-toluene mixture. The thrust of this experiment was to stabilize the peroxide and indicator combination through the use of the bicyclooctane derivative and the polyvinylpyrrolidone.

A second such method is disclosed in U.S. Pat. No. 3,853,471. This patent teaches the use of phosphoric or phosphonic acid amides where the substituent amido groups are primarily N-morpholine radicals.

Besides these attempts, there also exists the disclosure of U.S. Pat. No. 3,252,762 wherein the organic hydroperoxide is physically encapsulated within a colloidal material such as gelatin. Thus, when such a test strip is utilized, the aqueous test sample dissolves the gelatin capsules, thereby freeing the hydroperoxide for further reaction with the indicator in the presence of a peroxidatively active substance.

Each of these prior attempts was aimed at stabilizing the reagents so that the potentially incompatible reactive ingredients (hydroperoxide and indicator) would not prematurely combine and thereby render the test strips less sensitive. Hence, it can be said that the prior art methods were not directed towards the combined objectives of simultaneously enhancing stability and sensitivity, but rather they attempted to preserve existing sensitivity by preventing reagent decomposition during storage.

Another prior art reference which is of interest to the general concepts discussed herein in U.S. Pat. No. 3,236,850. This patent is directed towards stabilizing organic hydroperoxides used as catalysts and oxidizing agents. The patentees in this reference disclose the use of primary, secondary, or tertiary amine salts with organic peroxides. This reference is in no way directed toward reagent test strips.

Upon realizing that none of the above-described methods would achieve the kind of stability and sensitivity desired in a test strip for detecting peroxidatively active substances, the present inventor decided to take a completely different tack. This different approach was discovered during the research which led to the present invention, and resulted in a composition and device which completely fulfilled the desired objectives of increased stability and sensitivity.

But, even more surprisingly, yet another advantage resulted from this work — an improved method for preparing the device presently disclosed whereby the manufacture is dramatically simpler than processes enumerated in the foregoing prior art references — a one-dip method.

SUMMARY OF THE INVENTION

Briefly stated, the present invention relates to a test composition and device for detecting peroxidatively active substances, even after relatively long periods of storage. The composition which was discovered, and which meets these objectives, comprises an organic hydroperoxide, an indicator capable of producing a detectable response in the presence of a hydroperoxide and a peroxidatively active substance, and a borate ester having the structure

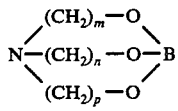

in which $m$, $n$ and $p$, which can be the same or different, are integers from 1 to about 4. The test device of the present invention comprises a carrier matrix which can be incorporated with the above test composition in a one-dip method.

DETAILED DESCRIPTION OF THE INVENTION

The organic hydroperoxide contemplated for use in the test composition can be selected from many well-known organic hydroperoxides. It must, however, be capable of reacting with a peroxidatively-sensitive indicator to produce a detectable response such as a color change or change in the amount of light absorbed or reflected by the test composition. Among hydroperoxides which have been found suitable are t-butyl hydroperoxide, cumene hydroperoxide, diisopropylbenzene, hydroperoxide, 2,5-dimethylhexane-2,5-dihydroperoxide, paramenthane hydroperoxide or mixtures thereof. Of these, cumene hydroperoxide has been found to be most preferable.

There exist many indicators which are capable of producing a detectable response in the presence of a hydroperoxide and a pseudoperoxidase, and which are, therefore, suitable for use in the present invention. For the most part, these include the so-called "benzidine-type" compounds. Typical of these are benzidine, o-tolidine, 3,3′5,5′-tetramethylbenzidine, 2,7-diaminofluorene or mixtures of these in varying proportions.

The borate esters which are presently believed to contribute to the increased stability and sensitivity of the present invention have the structure depicted above. Of the compounds included in this generic structure, it has been found that trimethanolamine borate, triethanolamine borate and tri(n-propanol)amine borate are particularly suitable. These compounds correspond to the above generic formula where $m$, $n$ and $p$ are the same integer and are 1, 2, or 3, respectively.

The amount of the borate ester useful in the present composition and device can vary broadly. This is reflected in the Examples, infra. Thus, in Example I the ratio of equivalents of triethanolamine borate to equivalents of cumene hydroperoxide present in the formulation is 4.71. Conversely, Example III evidences a 2.83 molar ratio of borate to hydroperoxide (1.4 equivalent ratio if the difunctionality of the peroxide is considered).

But the equivalent ratio range of about 1.4 to about 5, as shown in the Examples, is by no means limiting with respect to the amount of borate useful in the present invention. Any amount sufficient to achieve the desired degree of test composition stability and sensitivity can be employed, and this amount is easily determinable at the laboratory bench, given the present invention disclosure.

In a preferred embodiment of the present invention, the composition comprises cumene hydroperoxide, o-tolidine, and triethanolamine borate.

The test composition is typically prepared by dissolving or suspending portions of each ingredient in water or other suitable diluent or solvent. Other suitable diluents or solvents include chloroform, dimethylformamide, dimethylsulfoxide, and mixtures thereof in varying proportions.

The test device can be prepared by a one-dip process. Accordingly, a portion of a carrier matrix material is immersed in the solution and dried. Test devices thus prepared exhibit little loss in reactivity even after storage under stress conditions such as about 60° to about 70° C for 1 to 3 days and longer. By way of comparison, test devices were similarly prepared, but without the presence of the borate ester. When these strips were stored under substantially identical stress conditions, a dramatic loss in reactivity and sensitivity was observed.

The carrier matrix utilized in forming the test device can take a multitude of forms. Thus, U.S. Pat. No. 3,846,247 teaches the use of felt, porous ceramic strips, and woven or matted glass fibers. Additionally, U.S. Pat. No. 3,552,928 teaches the use of wood sticks, cloth, sponge material, and argillaceous substances. The use of synthetic resin fleeces and glass fiber felts as a carrier matrix is suggested in British Pat. No. 1,369,139. Another British Pat. No. 1,349,623, proposes the use of light-permeable meshwork of thin filaments as a cover for an underlying paper matrix. Polyamide fibers are taught in French Pat. No. 2,170,397. These suggestions notwithstanding, however, the material predominantly used in the art as a carrier matrix, and that which is especially suitable for the present invention, is a bibulous paper such as filter paper. It can thus be seen that there is a great deal of leeway in selecting an appropriate material for use as a carrier matrix, and the matrix can take various physical forms. All of these types are intended as being within the scope of the present invention.

The mechanism whereby the present approach to enhanced stability and sensitivity is realized is not known with certainty. However, the unique chemical characteristics of the borate ester utilized in the instant invention give rise to reasonable grounds for speculation. It is known that peroxides are generally unstable compounds, or at least less stable than most compounds occurring in nature. Some are explosive. Others, such as organic hydroperoxides (viz., cumene hydroperoxide), are relatively stable, but are believed to easily decompose in the presence of acids such as those present in occult blood-sensitive reagent formulations. When this decomposition occurs in the presence of an oxidizable indicator (such as those described herein) a redox reaction takes place. It is believed that this interaction may be the cause of observed decreased sensitivity of peroxidatively sensitive reagent strips with time.

On the other hand, borate esters such as those described herein are unique in the geometry of the nitrogen and boron atoms in the bicyclic structure, each comprising a separate bridgehead atom. The nitrogen atom at one bridgehead is electron-rich, containing an unshared pair of electrons projecting outwards from the molecular axis. The other bridgehead atom, the boron atom, situated at the other axial end of the molecule, is electron deficient and tends to coordinately bond with electron-rich anions.

Hence, because of its electron richness, the nitrogen end of the molecule could quite conceivably tie up a proton, whereas the electron-deficient boron bridgehead atom could coordinately couple with an anionic peroxide residue. Thus, it is believed that the unique electron distribution in the presently discussed bicyclic molecules stabilizes the organic peroxide in the present test composition by chemically inserting itself between the peroxidic proton and oxygen atoms, forming a coordinately coupled ion pair.

Thus, in the present test composition, the surprisingly increased stability is believed to arise from the organic hydroperoxide being precluded from ionically interacting with the indicator until the solvating power of the test sample destroys the peroxide-borate complex, and frees the peroxide to oxidize the indicator in the presence of a peroxidatively active substance.

In order to more clearly teach how to make and use the present invention, and to illustrate presently preferred embodiments thereof, the following examples are provided.

A. PREPARATION OF THE TEST COMPOSITION AND DEVICE

Example I — The Test Composition

A test composition was prepared by dissolving the following ingredients in 150 ml. (milliliters) deionized water. The ingredients were added to the water in descending order as listed.

| | |
|---|---|
| Trisodium citrate | 3.2 g (grams) |
| Citric Acid | 2.2 g |
| Ethylenediaminetetraacetic acid, tetrasodium salt | 0.1 g |
| Dimethylsulfone | 10.0 g |
| Sodium lauryl sulfate | 1.0 g |
| 6-Methoxyquinoline | 0.5 g |
| Dimethylsulfoxide | 25.0 ml |
| Acetone | 25.0 ml |
| Cumene hydroperoxide | 2.0 g |
| Triethanolamine borate (Aldrich Chemical Co., Inc.) | 10.0 g |
| o-tolidine | 0.4 g |

Example II — The Test Device

Strips of Whatmann 3MM filter paper were immersed in the test composition of Example I. The thus impregnated strips were dried at 70° C for about 15 minutes to form test composition-incorporated carrier matrices. The dried carrier matrices were then attached to plastic (polystyrene) strips or handles by means of double-faced adhesive tape purchased from 3M Company. The resulting test devices can be used to detect peroxidatively active substances by momentary immersion in a test sample, such as urine, suspected of containing such substance, and observing any development of color in the carrier matrix.

B. STABILITY TESTING OF VARIOUS TEST COMPOSITIONS

Example III

The purpose of this experiment was to compare the relative stabilities of several occult blood test compositions with that of the present invention. The following solution was prepared.

| | |
|---|---|
| chloroform | 100 ml |
| o-tolidine | 0.5 g |
| 2,5-dimethylhexane-2,5-dihydroperoxide | 2.0 g |
| poly(N-vinylpyrrolidone) | 10.0 g |

To aliquot portions of this solution (20 ml. each) were respectively added 1 gram of the additives in the following table. These test composition solutions were permitted to stand at room temperature for about 5 hours and the results observed are tabulated below.

| SAMPLE NO. | ADDITIVE | RESULTS |
|---|---|---|
| 1 | hexamethylenetetramine | Very dark, almost black solution. Not usable for occult blood analysis |
| 2 | 1,4-diazabicyclo-[2.2.2]octane | Dark green/brown discoloration Minimally sensitive to occult blood in urine. |
| 3 | triethanolamine borate | Slight browning. Relatively high sensitivity to occult blood in urine |
| 4 | control (no additive) | Turned black in about 2 hours. Unusable in occult blood analysis. |

C. THE STABILIZATION OF TEST DEVICES

Example IV — Control

A solution of the following test composition was prepared for preparation of a reagent strip sensitive to pseudoperoxidases. This formulation does not contain the borate ester component of the present invention.

| | |
|---|---|
| $H_2O$ | 150 ml |
| Trisodium Citrate | 3.2 g |
| Citric Acid | 2.2 g |
| Ethylenediaminetetraacetic acid, tetrasodium salt | 0.1 g |
| Dimethylsulfone | 10.0 g |
| Sodium lauryl sulfate | 1.0 g |
| 6-methoxyquinoline | 0.5 g |
| Dimethylsulfoxide | 25.0 ml |
| Acetone | 25.0 ml |
| Cumene hydroperoxide | 2.0 g |
| o-tolidine | 0.4 g |

A section of Whatmann 3MM filter paper was immersed in the above test composition solution and dried at 70° C. The dried paper was cut into 5mm squares, and these were attached to plastic handles using double-faced adhesive tape (available from 3M Company) thereby forming test devices.

Example V — Present Invention

A solution was prepared as in Example IV, above, except that 10g triethanolamine borate was added prior to the addition of the cumene hydroperoxide. Test devices were prepared from this solution in identical fashion as in Example IV.

Example VI — 1,4-diazabicyclo [2.2.2]octane

A solution was prepared as in Example IV, supra, except that 10g 1,4-diazabicyclo[2.2.2]octane was added prior to the addition of cumene hydroperoxide. This solution was used to prepare test devices in identical fashion as in Example IV.

Example VII — Hexamethylenetetramine

A solution was prepared as in Example IV, supra, except that 10g hexamethylenetetramine was added prior to the addition of cumene hydroperoxide. Test devices were prepared from this solution as in Example IV, supra.

Example VIII — Stability and Sensitivity Comparison

The test devices of Examples IV — VII were placed under stressed conditions to determine their relative stabilities and sensitivities. Devices from Examples IV — VI were stored for three days at about 60° C, and those of Example VII for one day at about 70° C. These stressed test devices were then tested for sensitivity by dipping in urine containing one part per million blood and observing any color change. Only the device containing triethanolamine borate (Example V) produced a change in color at this occult blood concentration (viz., 0.015 milligrams per deciliter). The remaining devices were insensitive to this level of occult blood.

D. PREFERRED EMBODIMENT

Example IX

The following ingredients are mixed in 150 ml water:

| | |
|---|---|
| Trisodium citrate | 3.2 g |
| Citric acid | 2.2 g |
| Ethylenediaminetetraacetic acid, tetrasodium salt | 0.1 g |
| Dimethyl sulfone | 10.0 g |
| Sodium lauryl sulfate | 1.0 g |
| 6-Methoxyquinoline | 0.5 g |
| Dimethylsulfoxide | 25.0 ml |
| Acetone | 25.0 ml |
| cumene hydroperoxide | 2.0 g |
| o-tolidine | 0.4 g |
| Triethanolamine borate | 10.0 g |

Strips of Whatmann 3MM filter paper were immersed in the above solution and dried at 70° C. When dried, the filter paper was cut into squares measuring 4 mm on a side. These squares were then mounted on polystyrene handles by use of double-faced adhesive tape (3M Company).

Test devices prepared in accordance with Example IX were stored at 60° C for three days and were found sensitive to occult blood in urine and concentrations as low as 0.015 milligram percent.

What is claimed is:

1. A test composition for detecting the presence of a peroxidatively active substance in a sample comprising
   an organic hydroperoxide,
   an indicator capable of producing a detectable response in the presence of a hydroperoxide and a peroxidatively active substance, and
   a borate ester having the structure

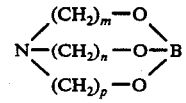

in which $m$, $n$ and $p$, same or different, are integers of 1 to about 4.

2. The composition of claim 1 in which the borate ester is trimethanolamine borate, triethanolamine borate, tri (n-propanol) amine borate, or mixtures thereof.

3. The composition of claim 1 in which the borate ester is triethanolamine borate.

4. The composition of claim 1 in which the indicator is benzidine, o-tolidine, 3,3',5,5'-tetramethylbenzidine, 2,7-diaminofluorene or mixtures thereof.

5. The composition of claim 1 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide or mixtures thereof.

6. The composition of claim 1 in which the organic hydroperoxide in cumene hydroperoxide.

7. The composition of claim 6 in which the borate ester is triethanolamine borate.

8. The composition of claim 6 in which the borate ester is trimethanolamine borate, triethanolamine borate, tri-(n-propanol) amine borate or mixtures thereof.

9. The composition of claim 8 in which the indicator is benzidine, o-tolidine, 3,3',5,5'-tetramethylbenzidine, 2,7-diaminofluorene or mixtures thereof.

10. A test composition for determining the presence of a peroxidatively active constituent in a sample, the composition comprising cumene hydroperoxide, o-tolidine, and triethanolamine borate.

11. A test device for determining the presence of a constituent in a sample wherein a carrier matrix is incorporated with a test composition comprising
    an organic hydroperoxide,
    an indicator capable of forming a detectable response in the presence of a hydroperoxide and a peroxidatively active substance, and
    a borate ester having the structure

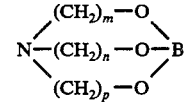

in which $m$, $n$ and $p$, same or different, are integers of 1 to about 4.

12. The device of claim 11 in which the borate ester is trimethanolamine borate, triethanolamine borate, tri(n-propanol) amine borate or mixtures thereof.

13. The device of claim 11 in which the borate ester is triethanolamine borate.

14. The device of claim 11 in which the indicator is benzidine, o-tolidine, 3,3',5,5'-tetramethylbenzidine, 2,7-diaminofluorene, or mixtures thereof.

15. The device of claim 11 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide of mixtures thereof.

16. The device of claim 11 in which the organic hydroperoxide is cumene hydroperoxide.

17. The device of claim 16 in which the borate ester is trimethanolamine borate, triethanolamine borate, tri-(n-propanol)amine borate or mixtures thereof.

18. The device of claim 16 in which the borate ester is triethanolamine borate.

19. The device of claim 18 in which the indicator is benzidine, o-tolidine, 3,3'5,5'-tetramethylbenzidine, 2,7-diaminofluorene, or mixtures thereof.

20. A test device for determining the presence of a peroxidatively active constituent in a sample, the device having a carrier matrix incorporated with a test composition comprising cumene hydroperoxide, o-tolidine and triethanolamine borate.

21. A one-dip process for preparing a test device for determining the presence of a peroxidatively active constituent in a sample comprising the steps of
preparing a mixture of a test composition comprising an organic hydroperoxide, an indicator capable of producing a detectable response in the presence of a hydroperoxide and a peroxidatively active substance, and a borate ester having the structure

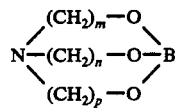

in which $m$, $n$ and $p$, same or different, are integers from 1 to about 4, and a suitable liquid diluent, and incorporating said mixture with a carrier matrix.

22. The process of claim 21 in which the borate ester is trimethanolamine borate, triethanolamine borate, tri (n-propyl)amine borate or mixtures thereof.

23. The process of claim 21 in which the borate ester is triethanolamine borate.

24. The process of claim 21 in which the indicator is benzidine, o-tolidine, 3,3',5,5'-tetramethylbenzidine, 2,7-diaminofluorene, or mixtures thereof.

25. The process of claim 21 in which the organic hydroperoxide is cumene hydroperoxide.

26. The process of claim 21 in which the organic hydroperoxide is t-butyl hydroperoxide, cumene hydroperoxide, diisopropylbenzene hydroperoxide, 2,5-dimethylhexane-2,5-dihydroperoxide, paramenthane hydroperoxide, or mixtures thereof.

27. The process of claim 26 in which the borate ester is trimethanolamine borate, triethanolamine borate, tri-(n-propanol)amine borate or mixtures thereof.

28. The process of claim 26 in which the borate ester is triethanolamine borate.

29. The process of claim 28 in which the indicator is benzidine, o-tolidine, 3,3',5,5'-tetramethylbenzidine, 2,7-diaminofluorene or mixtures thereof.

30. A one-dip process for preparing a test device for determining the presence of a peroxidatively active constituent in a sample, comprising the steps of
preparing a mixture of a test composition comprising cumene hydroperoxide, o-tolidine and triethanolamine borate, and a suitable liquid diluent, and incorporating the test compound with a matrix.

* * * * *